United States Patent [19]
Liu et al.

[11] Patent Number: 5,783,836
[45] Date of Patent: Jul. 21, 1998

[54] OPTICAL SENSOR APPARATUS FOR DETECTING VAPOR OF ORGANIC SOLVENT

[75] Inventors: Yuan Liu; Kenji Motosugi; Tetsu Yamamoto, all of Kawagoe, Japan; Christoph Roth, Munich, Germany; Masayuki Arai, Gyouda, Japan; Hans-Ulrich Simmrock, Sulzbach, Germany

[73] Assignee: Hoechst Aktiengesellschaft, Frankfurt, Germany

[21] Appl. No.: 579,833

[22] Filed: Dec. 28, 1995

[30] Foreign Application Priority Data

Dec. 28, 1994 [JP] Japan .................. 6-328281

[51] Int. Cl.$^6$ .................................. G01N 15/06
[52] U.S. Cl. .............. 250/574; 250/559.4; 73/335.01
[58] Field of Search .................. 250/573, 574, 250/575, 576, 559.4; 73/23.22, 23.31, 23.36, 24.04, 335.01, 335.02; 356/73, 409–412, 437; 435/166, 167, 172, 525, 169

[56] References Cited

U.S. PATENT DOCUMENTS

| 5,124,172 | 6/1992 | Burrell et al. | 436/525 |
| 5,268,145 | 12/1993 | Namba et al. | 436/169 |
| 5,308,771 | 5/1994 | Zhou et al. | 436/166 |

FOREIGN PATENT DOCUMENTS

| 0598341 | 5/1994 | European Pat. Off. . |
| 0674173 | 9/1995 | European Pat. Off. . |

OTHER PUBLICATIONS

Sensors and Actuators, vol. B17, No. 3, Feb. 1, 1994, pp. 203–209 entitled "Development of a Prototype Gas Sensor using Surface Plasmon Resonance on Gratings", by M.J. Jory.

GIT Fachz. vol. 34, No. 7, pp. 889–893 entitled "Dünne Polymerfilme Als Sensoren Für Kohlenwasserstoffe", by W. Nahm et al., Jan. 1990.

*Primary Examiner*—Que Le
*Attorney, Agent, or Firm*—Frommer Lawrence & Haug LLP

[57] ABSTRACT

An optical sensor apparatus for detecting a vapor of an organic solvent is characterized by a simple structure which allows easy manufacture, high reliability, low cost, compactness in size, and portability. The optical sensor apparatus has a light source unit which emits light for irradiating a polymer thin film formed on a flat reflecting substrate of a sensing element. Light reflected by the sensing element is detected by a light detecting unit. The light source unit, the sensing element, and the light detecting unit are integrally supported by a housing. The polymer thin film which comes into contact with a vapor of an organic solvent causes a change in the thickness and a reflective index thereof. This change is utilized to detect the existence and/or concentration of a vapor of an organic solvent.

6 Claims, 11 Drawing Sheets

OPTICAL SENSOR APPARATUS FOR DETECTING VAPOR OF ORGANIC SOLVENT

BACKGROUND OF THE INVENTION

1. Field of the Invention

The present invention relates to an apparatus for optically detecting the existence and/or concentration of a vapor of an organic solvent, and more particularly to an optical sensor apparatus for detecting a vapor of an organic solvent under analysis based on an interference enhanced reflection (IER) method by utilizing light reflected from a sensing element comprising a polymer thin film formed on a flat reflecting substrate which reacts with, absorbs or adsorbs the vapor.

2. Description of the Related Art

Optical sensors for detecting a vapor of an organic solvent based on the reflection of light have been announced by several individuals. One of the most recent examples is a proposal by Gauglitz et al who reported a reflection spectroscopy for detecting a gas or a vapor of a solvent by utilizing the swelling of a polymer thin film (GIT Fachz. Lab., 7, 889, 1990). This method uses a white light source and a spectrometer to analyze the spectra of reflectance, and measures a shift in wavelength in the reflection spectra as an indication of the concentration of a vapor.

U.S. Pat. No. 4,641,524 and DE-A-38 32 185 both disclose an optical humidity sensor using a dielectric mirror having a plurality of porous water-absorbent inorganic materials deposited on a transparent substrate. The porous water-absorbent inorganic material has the property of changing its refractive index when it absorbs water, so that the transmittance characteristic and reflection characteristic of the dielectric mirror vary with the change in humidity.

WO 83/023278 also discloses an optical humidity or vapor sensor using a dielectric interference mirror or an interference filter having a plurality of porous inorganic material layers laminated on a transparent substrate. Again in this sensor, the refractive index of the inorganic material varies with the change in humidity or vapor concentration, and a shift in wavelength of the dielectric interference mirror or interference filter is measured as an indication of relative humidity or vapor concentration.

The above-mentioned prior art techniques, however, are disadvantageous in that the method proposed by Gauglitz et al is complicated, and that equipment for implementing this method is expensive and bulky.

The sensors disclosed by U.S. Pat. No. 4,641,524, WO 83/023278 and DE-A-3 832 185 are limited to the detection of changes in refractive indices based on porous inorganic materials such as $TiO_2$, $SiO_2$, and so on. Moreover, the thickness of each layer must be substantially equal to $1/4n$ of the wavelength, where n represents the refractive index of an associated layer. Thus, constructing such a dielectric mirror requires a procedure which needs highly accurate and delicate treatments.

OBJECT AND SUMMARY OF THE INVENTION

The present invention has been proposed to overcome the foregoing problems, and a general object of the present invention is to provide an optical sensor apparatus for detecting the existence and/or concentration of a vapor of an organic solvent, an apparatus which is portable, small, inexpensive to manufacture and install, sensitive and highly responsive, and suitable for measuring a vapor of an organic solvent particularly in hazardous environments.

To achieve the above object, the present invention provides an optical sensor apparatus for optically detecting the existence and/or concentration of a vapor of an organic solvent, comprising:

a light source unit;

a sensing element comprising a polymer thin film formed on a flat reflecting plate and irradiated by the light emitted from the light source unit, the thin film changing a product of the thickness and the refractive index thereof when making contact with the vapor of the organic solvent;

a light detecting unit for detecting the light reflected by the sensing element; and a housing for supporting the light source unit, the sensing element and the light detecting unit.

The present invention takes advantage of the fact that a polymer thin film changes in thickness and/or refractive index due to swelling thereof, enabling detection of a vapor of an organic solvent by measuring a change in the reflecting characteristic of a sensing element which comprises the polymer thin film formed on a flat reflecting substrate. The polymer thin film interacts with a particular chemical substance or several kinds of chemical substances belonging to a certain category. The interaction results in physical changes in the polymer thin film such as swelling or the like. Further, the swelling causes changes in the thickness and the refractive index of the polymer thin film, which serve as optical parameters thereof. Since various changes like these cause the optical reflective property of the polymer thin film to change, a vapor of an organic solvent can be detected by measuring changes in the reflection characteristics of the polymer thin film or sensing element. The present invention employs an IER method as a means for measuring such changes in the reflection characteristics. Specifically, the present invention detects changes in the product of the thickness and refractive index of the polymer thin film caused by a reaction of the polymer thin film with a chemical substance or by the polymer thin film absorbing or adsorbing the chemical substance preferably by means of a measuring means which implements the IER method.

The present invention provides a method which takes advantage of the reflection characteristics of a polymer thin film formed on a highly reflecting substrate. Light reflected from the surface of the polymer thin film and light reflected from the interface between the polymer thin film and the substrate interfere with each other. The intensity of reflected light largely depends on the thickness and refractive index of the polymer thin film. In other words, a change in the thickness or refractive index of the polymer thin film or changes in both factors appear as a change in the intensity of reflected light. Even if a plurality of polymer thin films exhibit different swelling behaviors, the swelling of the respective polymer thin films can be readily identified from changes in the intensities of light reflected from the respective polymer thin films. The IER method thus takes advantage of changes in the thickness and/or refractive index, particularly changes in the thickness of the polymer thin film as physical changes in the polymer thin film for detecting organic solvents. The present invention relies on the IER method to detect the existence and/or concentration of chemical substances as a function of the intensity of reflected light.

The present invention enables different kinds of organic solvents to be distinguished from each other by measuring changes in intensity of reflected light or changes in response time caused by variations in the thickness and refractive index of the polymer thin film due to the swelling thereof.

In other words, interactions between a polymer thin film and an organic solvent are different depending on the kind of the polymer thin film as well as the kind and concentration of the organic solvent, so that the intensity of reflected light produced by the interaction is also different depending on a combination of the polymer thin film and the organic solvent. A response time also varies in accordance with the degree of the interaction between the polymer thin film and the organic solvent. Thus, it is possible to distinguish different kinds of organic solvents from each other from information such as the intensity of reflected light, a change in response time, and so on. In the present invention, for simultaneously detecting and identifying different organic solvents, the same kind of sensing elements or different kinds of sensing elements can be employed.

According to the present invention, the light source unit may comprise a visible or infrared laser diode or light emitting diode (LED). The light detecting unit may be formed of a photo-diode or photo-transistor. Furthermore, the light source and photo-detector can be implemented in a single integrated device.

Also, the optical sensor apparatus according to the present invention includes a housing for holding the sensing element in communication with the light source unit and the light detecting unit. The housing includes a vapor inlet for introducing a vapor of an organic solvent, a vapor outlet for exhausting the vapor of the organic solvent, and a passage for interconnecting vapor inlet and vapor outlet and for causing the vapor of the organic solvent to come into contact with the polymer thin film. In a first embodiment, the light source unit and the light detecting unit are positioned in the housing so as to face the polymer thin film. Light emitted from the light source unit is therefore received by the polymer thin film and reflected toward the light detecting unit. In a second embodiment, the light source unit includes a light emitting element, a first optical fiber having one end coupled to the light emitting element for carrying light emitted from the light emitting element, and an irradiating member coupled to the other end of the first optical fiber for irradiating the polymer thin film with the light from the light emitting element. The light detecting unit includes a light receiving member for receiving light reflected from the polymer thin film, a second fiber having one end coupled to the light receiving member for carrying the light received by the light receiving member, and a photo-detector coupled to the other end of the second optical fiber.

According to the present invention, light emitted from the light source unit is preferably directed to the polymer thin film at an arbitrary incident angle of less than 90 degrees. The output of the optical sensor apparatus according to the present invention is supplied to an associated electronic circuit which in turn generates an appropriate electric signal indicative of the existence and/or concentration of a vapor of an organic solvent under detection.

DESCRIPTION OF THE PREFERRED EMBODIMENTS

Figure 1:
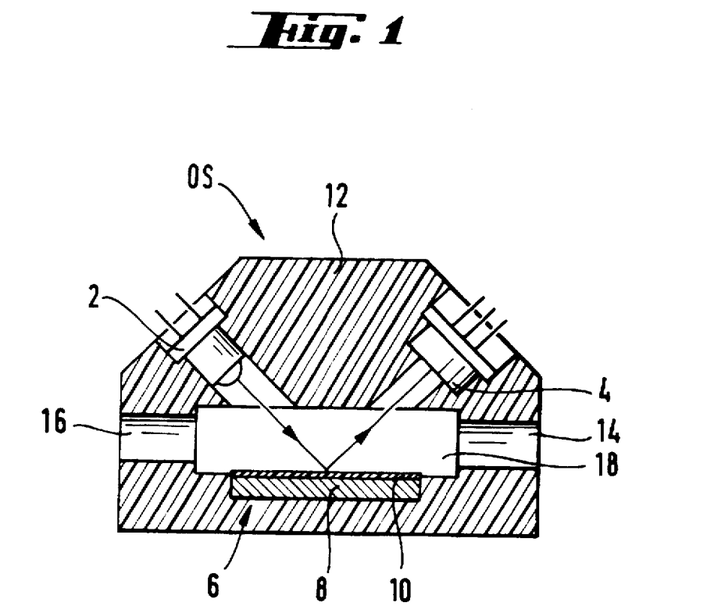
FIG. 1 is a cross-sectional view showing the structure of a first embodiment of an optical sensor apparatus according to the present invention.

FIG. 1 shows the structure of a first embodiment of an optical sensor apparatus according to the present invention. In FIG. 1, an optical sensor apparatus OS comprises a light source unit 2, a light detecting unit 4, and a sensing element 6 including a polymer thin film 10 formed on a flat reflecting substrate 8. These components are integrally held in a housing 12 made of plastic or metal. Light source unit 2, which has a light emitting element, for example, a laser diode, LED or the like, which emits a light beam, generates a visible light beam or an infrared beam which impinges on polymer thin film 10 at an incident angle of less than 90 degrees. The light beam reflected by polymer thin film 10 is received by a photo-detector of light detecting unit 4. Light detecting unit 4 may comprise a photo-diode or a photo-transistor which is suitable for detecting light beams from light source unit 2.

The light beam generated from light source unit 2 may be polarized light or non-polarized light. When polarized light is used, the light beam preferably has a polarized plane perpendicular to the plane of incidence. In addition, for higher sensitivity, a large incident angle, for example, 50 degrees or more is preferable. On the other hand, when non-polarized light is used, a smaller incident angle, for example, 10–30 degrees is preferable.

Housing 12 is formed with a vapor inlet 14 for introducing a vapor of an organic solvent thereinto, a vapor outlet 16 for exhausting the vapor of the organic solvent therefrom, and a passage 18 for interconnecting vapor inlet 14 with vapor outlet 16 for causing the vapor to come into contact with polymer thin film 10. The vapor of the organic solvent is introduced through vapor inlet 14 into housing 12 by suction, inflow or diffusion, and comes into contact with polymer thin film 10 as it passes through passage 18, and is exhausted from vapor outlet 16.

The output from light detecting unit 4 is supplied to an appropriate electric circuit (described later) to generate an electric signal representing the existence and/or concentration of a vapor of an organic solvent under detection.

Figure 2:
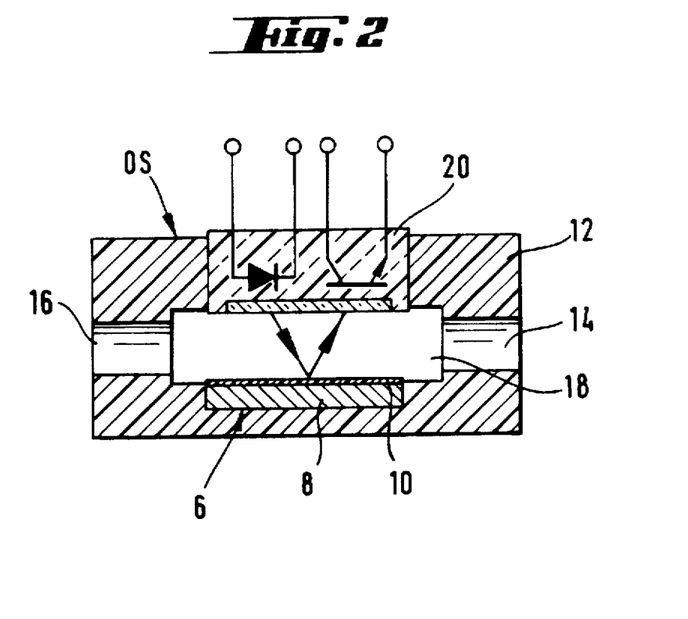
FIG. 2 is a cross-sectional view showing the structure of a second embodiment of the optical sensor apparatus according to the present invention.
Figure 3A:
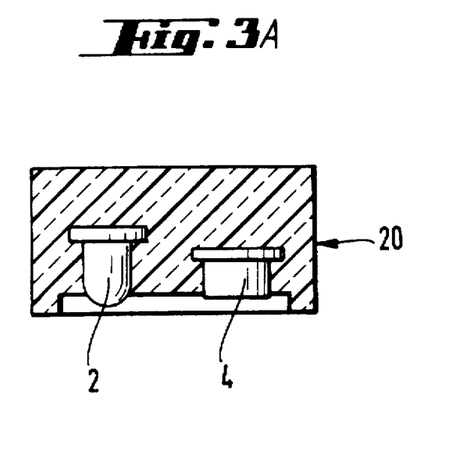
FIGS. 3A and 3B are cross-sectional views respectively showing an exemplary structure of an integrated device used in the optical sensor apparatus of FIG. 2.
Figure 3B:
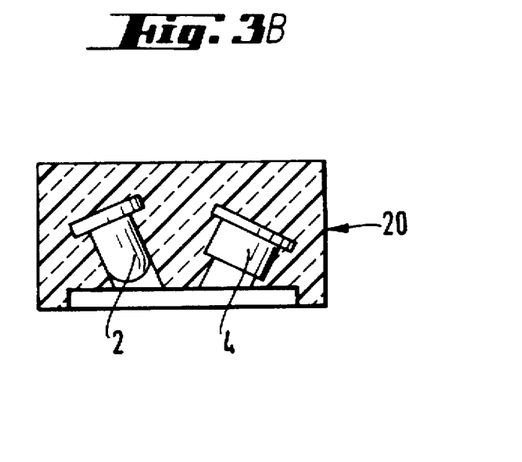

FIG. 2 shows the structure of a second embodiment of an optical sensor apparatus according to the present invention. The second embodiment differs from the first embodiment in that the former comprises an integrated circuit 20 which integrally includes a light source and a photo-detector. Integrated circuit 20 may comprise a photo-reflector or a photo-interrupter which is a combination of a light emitting diode (LED) as a light emitting element and a photo-transistor as a photo-detector, by way of example. In this case, light source unit 2 and light detecting unit 4 may be disposed in integrated circuit 20 in such a manner that light source unit 2 and light detecting unit 4 are in parallel with each other as shown in FIG. 3A or they form an angle as shown in FIG. 3B.

Figure 4:
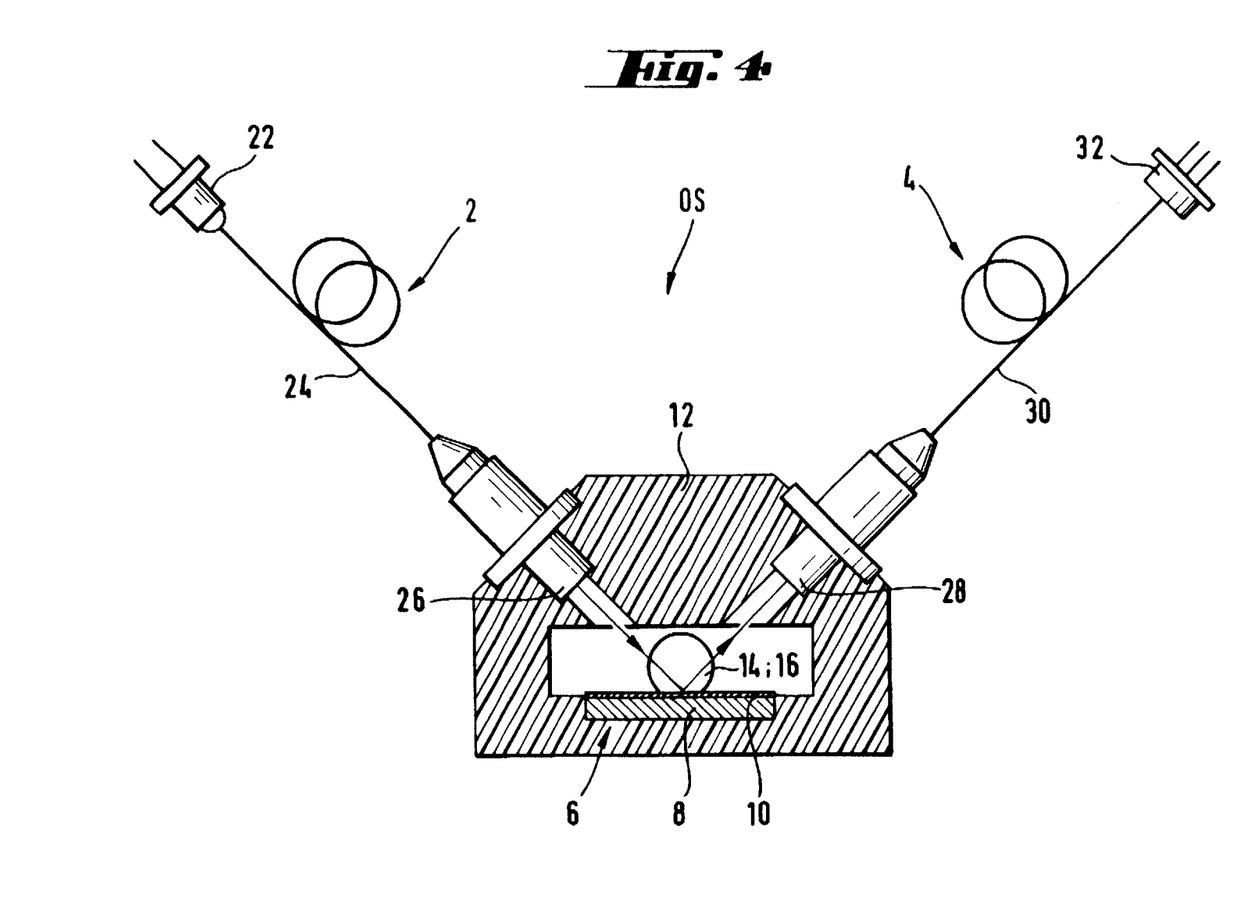
FIG. 4 is a cross-sectional view showing the structure of a third embodiment of the optical sensor apparatus according to the present invention.

FIG. 4 shows the structure of a third embodiment of an optical sensor apparatus according to the present invention. In this embodiment, light source unit 2 comprises a light emitting element 22, an input optical fiber 24 having one end coupled to light emitting element 22 and fixed to housing 12, and an irradiating member 26 coupled to the other end of input optical fiber 24. A light beam emitted from light emitting element 22 is transmitted to irradiating member 26 through input optical fiber 24 so that polymer thin film 10 is irradiated with the light beam by irradiating member 26. Correspondingly light detecting unit 4 comprises a light receiving member 28 fixed to housing 12 so as to receive a light beam reflected from polymer thin film 1 or an output optical fiber 30 for transmitting the light beam received by light receiving member 28, and a photo-detector 32 for detecting the light beam transmitted through output optical fiber 30. Irradiating member 26 has a lens for converging the light beam transmitted from input optical fiber 24 on polymer thin film 10. Light receiving member 28 preferably has a collimator for collimating the light reflected by thin film 10 for transmission through output optical fiber 30.

Irradiating member 26 is positioned such that a light beam transmitted through input optical fiber 24 irradiates polymer thin film 10 at a desired incident angle. Light receiving member 28 is positioned so as to appropriately receive a light beam reflected from polymer thin film 10 and transmit it to output optical fiber 30.

Figure 5:
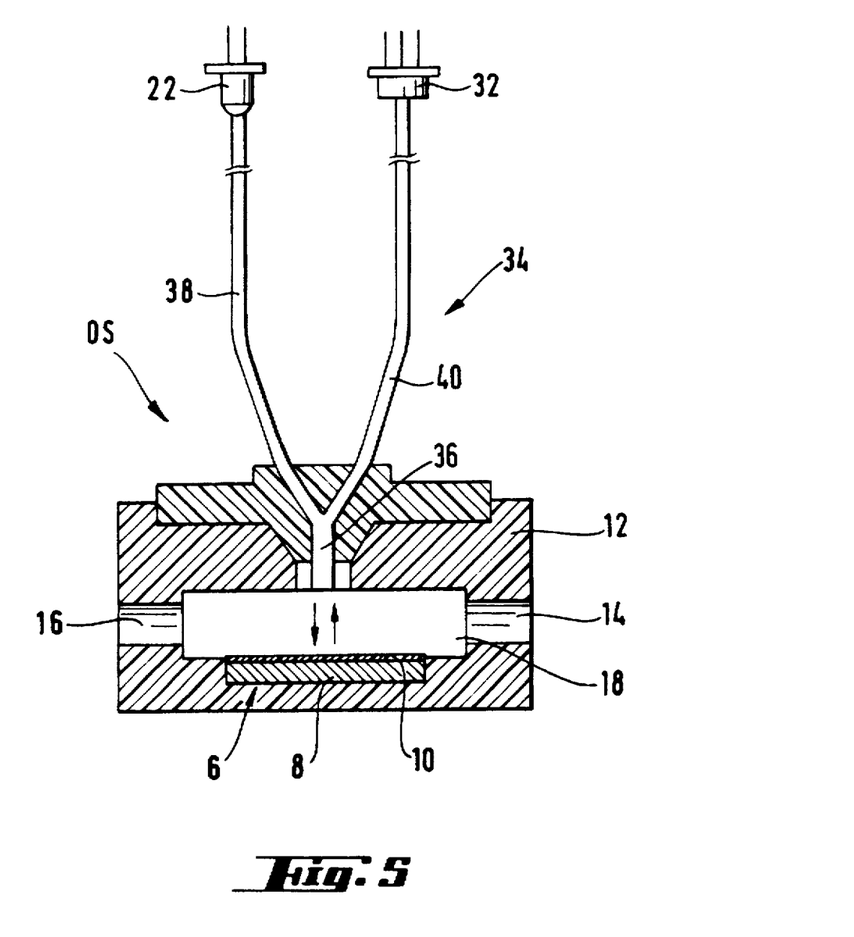
FIG. 5 is a cross-sectional view showing the structure of a fourth embodiment of the optical sensor apparatus according to the present invention.

FIG. 5 shows the structure of a fourth embodiment of an optical sensor apparatus according to the present invention. This embodiment employs a bifurcated (i.e., a Y-coupled) optical fiber (which may also be called a light guide or a fiber bundle) 34. Bifurcated optical fiber 34 includes two branch fibers 38, 40 which are coupled at a junction end 36. Junction end 36 is positioned perpendicularly to and above polymer thin film 10 with a predetermined spacing therebetween, in such a manner that a light beam from light emitting element 22 transmitted through one branch 38 of bifurcated fiber 34 impinges on polymer thin film 10 at a right angle. The light beam reflected by polymer thin film 10 is received by junction end 36 and transmitted to photo-detector 32 through other branch 40 of bifurcated fiber 34.

In this structure, optical fiber 34 may be a single mode optical fiber, a multi-mode optical fiber, or an optical fiber light guide formed of an array of single mode optical fibers or multi-mode optical fibers. Junction end 36 may be provided with a lens for converging a light beam from branched fiber 38 and a collimator for collimating a light beam reflected from polymer thin film 10. Also, a polarizer may be provided for producing a polarized beam. Further, a light beam splitter may be provided in order to generate a reference beam required to monitor fluctuations in the intensity of the light beam.

In the foregoing embodiments, polymer thin film 10 formed on flat reflecting substrate 8 reacts with, absorbs or adsorbs a vapor of an organic solvent under measurement. As a result, such interaction causes polymer thin film 10 to change in film thickness and/or refractive index. Particularly, polymer thin film 10 has the property of swelling through an interaction with an organic solvent vapor under measurement, which results in a change in the thickness and/or refractive index of polymer thin film 10. Thus, by appropriately selecting a polymer material for polymer thin film 10, it is possible to selectively or non-selectively detect vapors of most organic solvents including normal hydrocarbon, halogenated hydrocarbon, alcohol, ketone, ester, ether, amide, amine, and so on.

Substrate 8 for supporting polymer thin film 10 is preferably flat enough to reflect light and preferably has a high reflectivity. Substrate 8 may be made of, for example, a silicon wafer. Polymer thin film 10 may be formed on the surface of substrate 8 by a spin coat method or any other generally used costing method.

The present invention utilizes the aforementioned IER method to detect a change in the thickness and/or refractive index of polymer thin film 10. The IER method takes advantage of the optical interference characteristic of a thin film structure. Specifically, light reflected from the surface of polymer thin film 10 has a phase relationship with light reflected from the interface between polymer thin film 10 and substrate 8, and they interfere with each other. The reflectivity of the sensing element largely depends on the thickness and refractive index of the polymer thin film. In other words, a change in the thickness and/or refractive index will result in a change in the reflectivity of the polymer thin film or the intensity of light reflected from the polymer film. Thus, the IER method enables the existence and/or concentration of an organic solvent vapor to be detected as a function of the intensity of light reflected from the polymer thin film.

Figure 6:
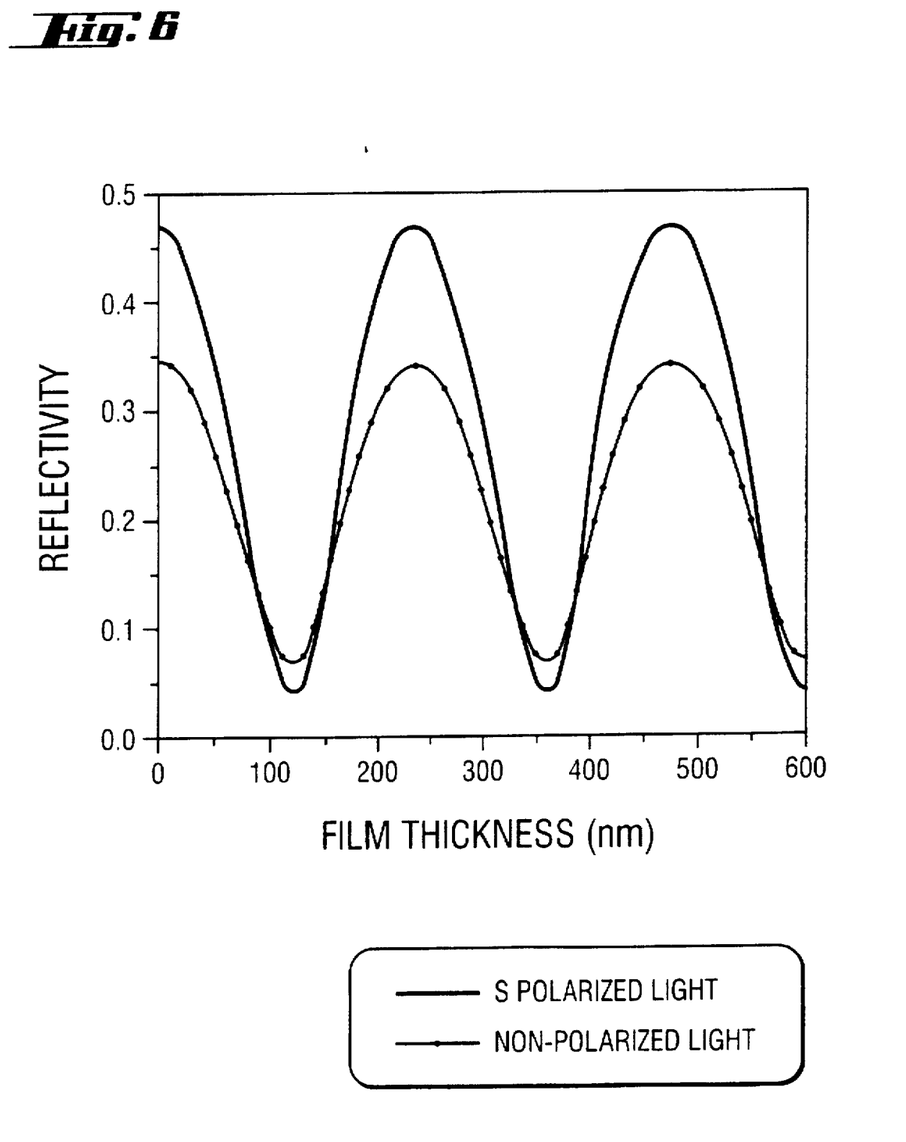
FIG. 6 is a graph showing calculated reflectivities of a polymer thin film as a function of the thickness of the polymer thin film when polarized light and non-polarized light are incident on the polymer thin film at an incident angle of 45 degrees.

It should be noted that the IER method is particularly sensitive to changes in the thickness of the polymer thin film. On the other hand, considering that the refractive index of an organic solvent vapor is not so different from that of polymer thin film 10 used in the present invention, a change on reflective index of polymer thin film 10 caused by absorption of an organic vapor is very small, while the corresponding change in thickness is much more significant. This change in thickness is utilized to detect vapors of organic solvents. This is a unique advantage of the present invention over the prior art. Another point to be emphasized in comparison of the present invention with the prior art is related to the thickness of polymer thin film 10. FIG. 6 shows reflectivities of a polymer thin film having a refractive index of 1.5 formed on a silicon substrate, which is calculated as a function of the thickness of the polymer thin film when polarized light and non-polarized light are incident on the polymer thin film at an incident angle of 45 degrees. The wavelength of the polarized light and non-polarized light used herein was selected to be 633 nm. It can be seen from the curves in FIG. 6 that the thickness of the polymer thin firm suitable for the IER method employed by the present invention preferably takes values except for those near integer multiples of $\lambda/4n\cos\theta$ corresponding to minimum values and maximum values of the reflectivity curves, where $\lambda$ is the wavelength of the used polarized light and non-polarized light, n is the refractive index of the polymer thin film, and θ is a light propagation angle within the polymer thin film. This is because the reflectivity near a minimum value or a maximum value of the reflectivity curve is less sensitive to changes in thickness or refractive index of the polymer thin film. While the thickness of the polymer thin film may range from 10 nm to 10 μm, a thickness less than 1 μm is preferable in view of a high speed response.

Figure 7:
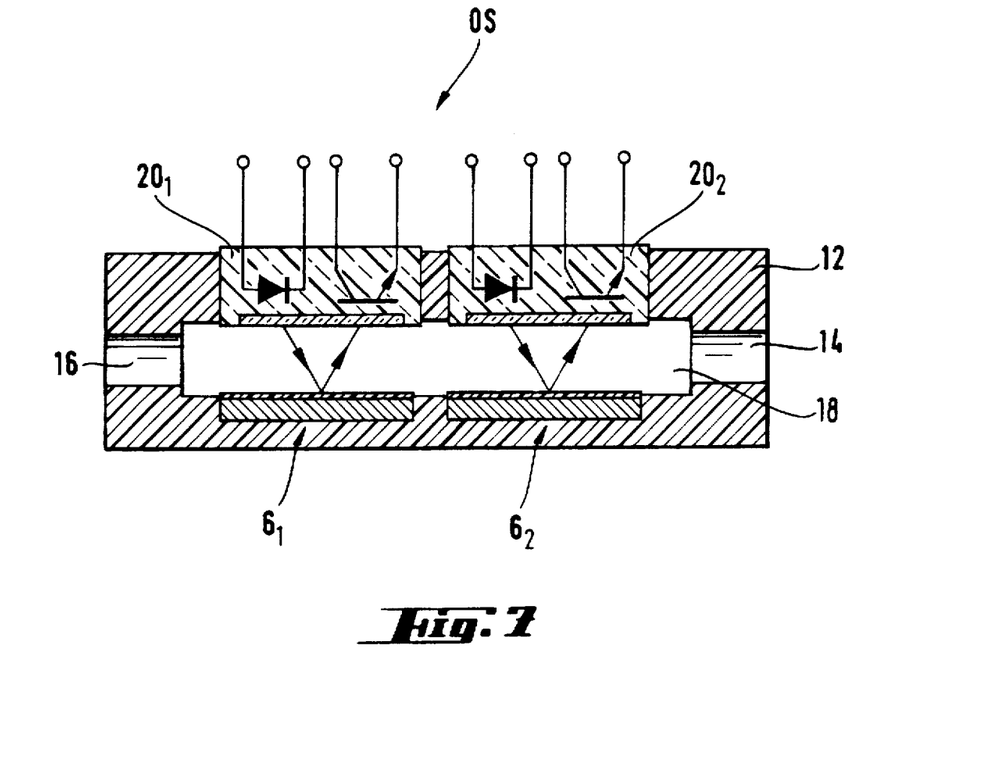
FIG. 7 is a cross-sectional view showing the structure of a fifth embodiment of the optical sensor apparatus according to the present invention which comprises a plurality of sensing elements, a plurality of light source units, and a plurality of light detecting units.

In the first to fourth embodiments described hereinabove, optical sensor apparatus OS has a set of light source unit 2, light detecting unit 4 and sensing element 6. Alternatively, a plurality of such sets, if provided in housing 12 will enable simultaneous detection of different organic solvent vapors, selective detection of a particular organic solvent vapor and compensation for the influences of temperature, humidity and other attendant factors. FIG. 7 shows the structure of a fifth embodiment of an optical sensor apparatus according to the present invention which includes two such sets along passage 18, where a first set has an integrated device $20_2$ and a sensing element $6_1$, and a second set has an integrated device $20_2$ and a sensing element $6_2$.

In the foregoing first to fifth embodiments, polymer thin film 10 is preferably a homopolymer or copolymer having a recurring unit represented by the following chemical formula (I)

where

X represents —H, —F, —Cl, —Br, —CH$_3$, —CF$_3$, —CN, or —CH$_2$—CH$_3$;

R$^1$ represents —R$^2$ or —Z—R$^2$;

Z represents —O—, —S—, —NH—, —NR$^{2'}$—, —(C=Y)—, —(C=Y)—Y—, —Y—(C=Y)—, —(SO$_2$)—, —Y'—(SO$_2$)—, —(SO$_2$)—Y'—, —Y'—(SO$_2$)—Y'—, —NH—(C=O)—(C=O)—NH—, —(C=O)—NR$^{2'}$—, —Y'—(C=Y)—Y'—, or —O—(C=O)—(CH$_2$)n—(C=O)—O—;

Y independently represents O or S;

Y' independently represents O or NH;

n represents an integer ranging from zero to 20;

R$^2$ and R$^{2'}$ independently represent hydrogen atom, a linear alkyl group, a branched alkyl group, a cycloalkyl group, an unsaturated hydrocarbon group, an aryl group, a saturated or unsaturated hetero ring, or derivatives thereof.

It should be noted that R' does not represent hydrogen atom, linear alkyl group, or branched alkyl group.

It is particularly preferable to use homopolymer or copolymer having the recurring unit represented by the above chemical formula (I), where X represents H or CH$_3$;

R$^1$ represents substituted or unsubstituted aryl group or —Z—R$^2$;

Z represents —O—, —(C=O)—O—, or —O—(C=O)—; and

R$^2$ represents a linear alky group, branched alkyl group, cycloalkyl group, unsaturated hydrocarbon group, aryl group, saturated or unsaturated hetero ring, or derivatives thereof.

Polymer used as the polymer thin film for the present invention may be a polymer consisting of a single recurring unit (I), a copolymer consisting of another recurring unit and the above-mentioned recurring unit (I), or a copolymer consisting of two or more species of the recurring unit (I). The recurring units in the copolymer may be arranged in any order, and a random copolymer, alternate copolymer, block copolymer or graft copolymer may be used by way of example. Particularly, the polymer thin film is preferably made from polymethacrylic acid esters or polyacrylic acid esters. The side-chain group of the ester is preferably a linear or branched alkyl group, or cycloalkyl group with the number of carbon molecules ranging preferably from 4 to 22.

Polymers particularly preferred for the polymer thin film are listed as follows:

poly(dodecyl methacrylate);
poly(isodecyl methacrylate);
poly(2-ethylhexyl methacrylate);
poly(2-ethylhexyl methacrylate-co-methyl methacrylate);
poly(2-ethylhexyl methacrylate-co-styrene);
poly(methyl methacrylate-co-2-ethylhexyl acrylate);
poly(methyl methacrylate-co-2-ethylhexyl methacrylate);
poly(isobutyl methacrylate-co-glycidyl methacrylate);
poly(cyclohexyl methacrylate);
poly(octadecyl methacrylate);
poly(octadecyl methacrylate-co-styrene);
poly(vinyl propionate);
poly(dodecyl methacrylate-co-styrene);
poly(dodecyl methacrylate-co-glycidyl methacrylate);
poly(butyl methacrylate);
poly(butyl methacrylate-co-methyl methacrylate);
poly(butyl methacrylate-co-glycidyl methacrylate);
poly(2-ethylhexyl methacrylate-co-glycidyl methacrylate);
poly(cyclohexyl methacrylate-co-glycidyl methacrylate);
poly(cyclohexyl methacrylate-co-methyl methacrylate);
poly(benzyl methacrylate-co-2-ethylhexyl methacrylate);
poly(2-ethylhexyl methacrylate-co-diacetoneacrylamide);
poly(2-ethylhexyl methacrylate-co-benzyl methacrylate-co-glycidyl methacrylate);
poly(2-ethylhexyl methacrylate-co-methyl methacrylate-co-glycidyl methacrylate);
poly(vinyl cinnamate);
poly(vinyl cinnamate-co-dodecyl methacrylate);
poly(tetrahydrofurfuryl methacrylate);
poly(hexadecyl methacrylate);
poly(2-ethylbutyl methacrylate);
poly(2-hydroxyethyl methacrylate);
poly(cyclohexyl methacrylate-co-isobutyl methacrylate);
poly(cyclohexyl methacrylate-co-2-ethylhexyl methacrylate);
poly(butyl methacrylate-co-2-ethylhexyl methacrylate);
poly(butyl methacrylate-co-isobutyl methacrylate);
poly(cyclohexyl methacrylate-co-butyl methacrylate);
poly(cyclohexyl methacrylate-co-dodecyl methacrylate);
poly(butyl methacrylate-co-ethyl methacrylate);
poly(butyl methacrylate-co-octadecyl methacrylate);
poly(butyl methacrylate-co-styrene);
poly(4-methyl styrene);
poly(cyclohexyl methacrylate-co-benzyl methacrylate);

poly(dodecyl methacrylate-co-benzyl methacrylate);

poly(octadecyl methacrylate-co-benzyl methacrylate);

poly(benzyl methacrylate-co-tetrahydrofurfuryl methacrylate);

poly(benzyl methecrylate-co-hexadecyl methacrylate);

poly(dodecyl methacryiate-co-methyl methacrylate);

poly(dodecyl methacrylate-co-ethyl methacrylate);

poly(2-ethylhexyl methacrylate-co-dodecyl methacrylate);

poly(2-ethylhexyl methacrylate-co-octadecyl methacrylate);

poly(2-ethylbutyl methacrylate-co-benzyl methacrylate);

poly(tetrahydrofurfuryl methacrylate-co-glycidyl methacrylate);

poly(styrene-co-octadecyl acrylate);

poly(octadecyl methacrylate-co-glycidyl methacrylate);

poly(4-methoxystyrene);

poly(2-ethylbutyl methacrylate-co-glycidyl methacrylate);

poly(styrene-co-tetrahydrofurfuryl methacrylate);

poly(2-ethylhexyl methacrylate-co-propyl methacrylate);

poly(octadecyl methacrylate-co-isopropyl methacrylate);

poly(3-methyl-4-hydroxystyrene-co-4-hydroxystyrene);
poly(styrene-co-2-ethylhexyl methacrylate-co-glycidyl methacrylate);

It should be noted that in the methacrylate acid ester polymers or copolymers listed above, acrylic acid may be substituted for methacrylate acid. The polymers may be crosslinked on their own, or they can be crosslinked by introducing compounds that have crosslinking reactive groups. Suitable crosslinking reactive groups include, for example, an amino group, a hydroxyl group, a carboxyl group, an epoxy group, a carbonyl group, an urethane group and derivatives thereof. Other examples include maleic acid, fumaric acid, sorbic acid, itaconic acid, cinnamic acid and derivatives thereof. Also useful as crosslinking agents may be those substances which have chemical structures that are capable of forming carbenes or nitrenes upon exposure to visible or ultraviolet light or high energy radiation. Since the films formed from crosslinked polymers are insoluble to organic vapors, the stability of the optical sensor apparatus can be enhanced by crosslinking a polymer from which the polymer thin film of the optical sensor apparatus is formed. The methods of crosslinking are not limited in any particular way and various known crosslinking techniques, such as thermal process and exposure to light or high energy radiation, can be employed.

Next, various examples of detecting vapors of various hydrocarbons, made with the optical sensor apparatus according to the present invention, will be explained with reference to FIGS. 8–11.

EXAMPLES

Example 1

Figure 8:
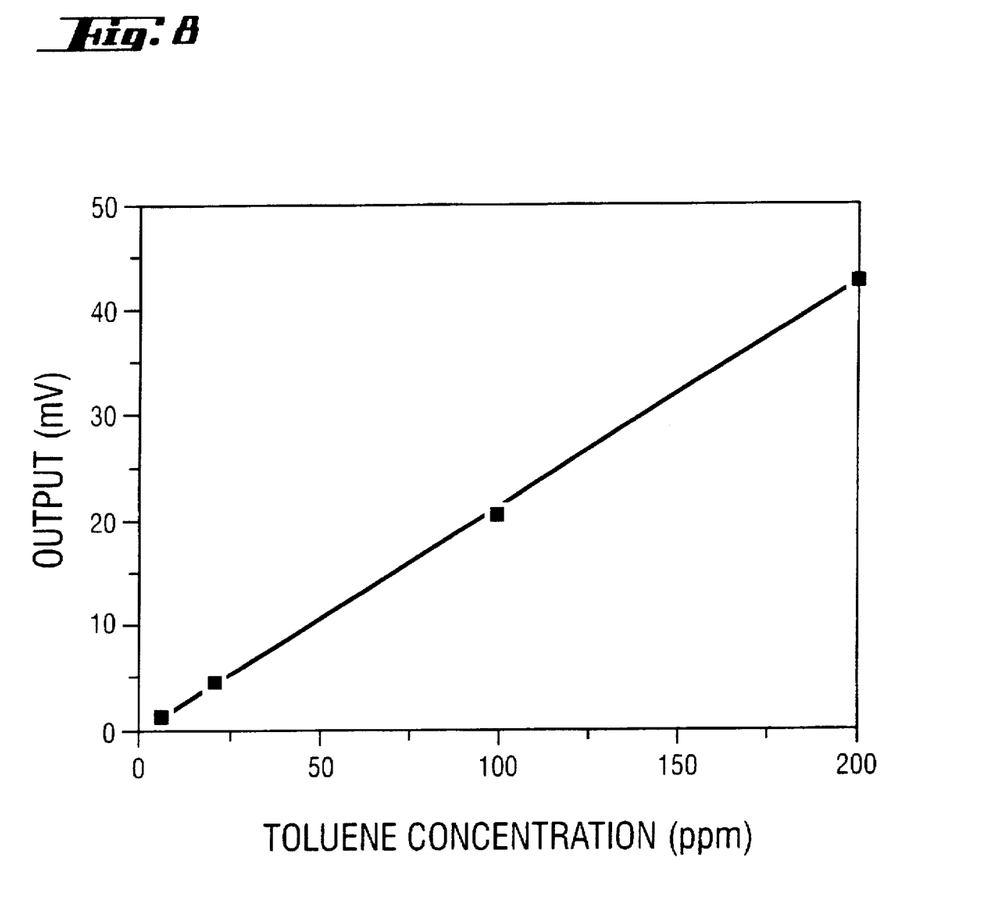
FIG. 8 is a graph showing the result of measurements made by the optical sensor apparatus of the present invention when used to detect a low concentration toluene vapor.

FIG. 8 is a graph showing the result of measurements of a low concentration toluene vapor using optical sensor apparatus OS according to the present invention. The measurements were made using optical sensor apparatus OS which has the same structure as that shown in FIG. 1. Sensing element 6 has polymer thin film 10 of poly (octadecyl methacrylate-co-glycldyl methacrylate) spin coated onto silicon substrate 8. The polymer thin film has a thickness of about 2 μm. A toluene vapor in various concentrations is introduced into housing 12 by means of suction and comes into contact with polymer thin film 10. Light source unit 2 is a laser diode which emits light at a wavelength of 830 nm. Light from the laser diode is directed to polymer thin film 10 at an incident angle of 67.5 degrees. The light reflected from polymer thin film 10 is then monitored with light detecting unit 4 including a silicon photo-diode, and the output of the photo-diode is fed to an associated electronic circuitry to produce a signal denoting the concentration of the toluene vapor. It can be seen from the graph of FIG. 8 that optical sensor apparatus 10 shows a high sensitivity in a concentration range less than 20 ppm with a linear response to the toluene concentrations in the range from 0 to 200 ppm.

Example 2

Figure 9:
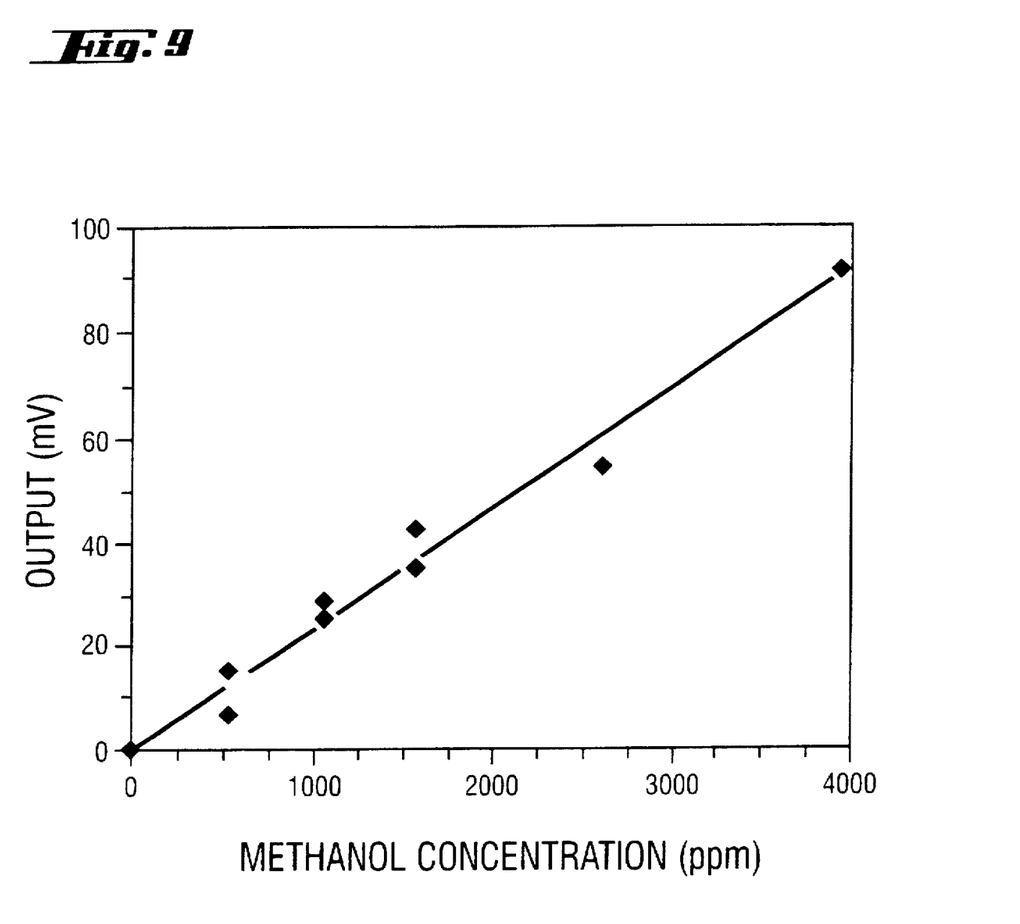
FIG. 9 is a graph showing the result of measurements made by the optical sensor apparatus of the present invention when used to detect a methanol vapor.

FIG. 9 shows the result of measurements of a methanol vapor obtained under similar conditions as in Example 1. A condition of Example 2 differs from Example 1 in that Example 2 uses polymer thin film 10 which is a film of poly(4-hydroxy styrene) having a thickness of 370 nm. It can be seen from the graph of FIG. 9 that optical sensor apparatus OS has a linear response to methanol concentrations in the range from 0 to 4000 ppm.

Example 3

Figure 10:
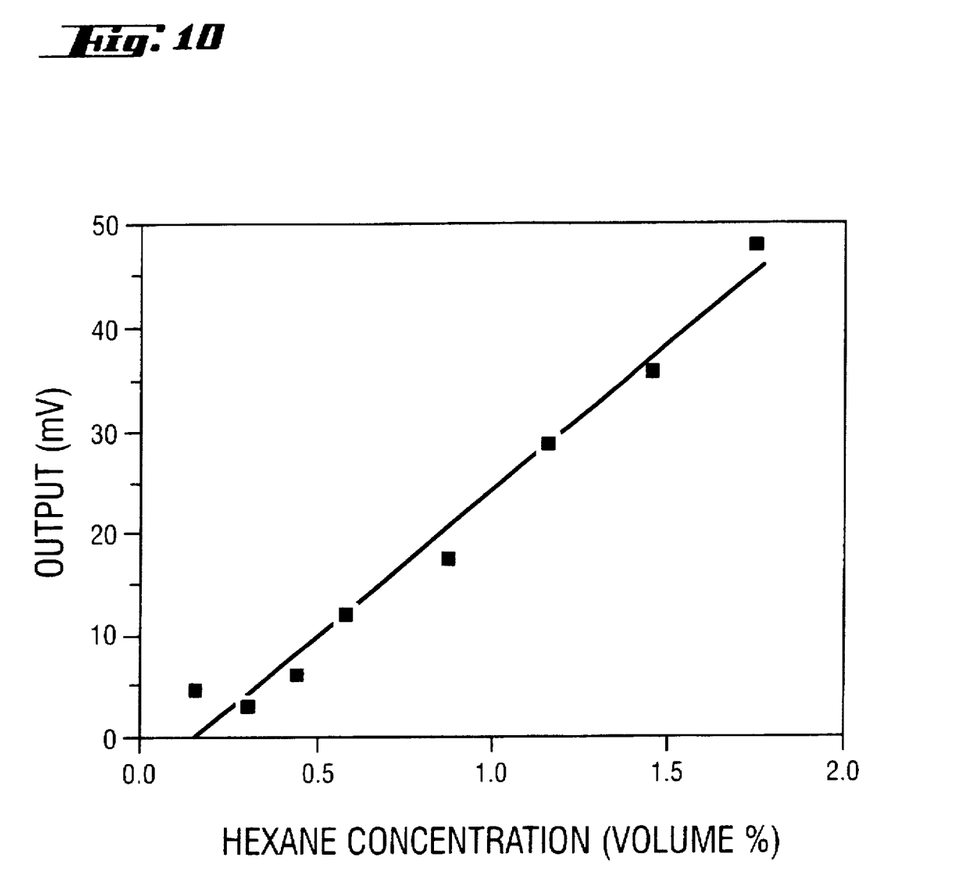
FIG. 10 is a graph showing the result of measurements made by the optical sensor apparatus of the present invention when used to detect a high concentration hexane vapor.

FIG. 10 shows an example of measurements of a high concentration vapor of hexane, using optical sensor apparatus as having the same structure as shown in FIG. 2. Optical sensor apparatus OS uses a photo-reflector (P2826 made by Hamamatsu Photonics Co.) which includes a LED light source and a photo-transistor separated from each other by 2.1 mm. The LED in P2826 emits light having a peak wavelength of 940 nm and a full spectrum width at half maximum of 54 nm. The P2826 photo-reflector is placed 3 mm above sensing element 6 such that the light from the LED is incident on polymer thin film 10 at an incident angle of 19.3 degrees. Polymer thin film 10 of sensing element 6 is made of 2-ethythexyl methacrylate and benzyl methacrylate and has a thickness of 200 nm. Optical sensor apparatus OS responds linearly to a lower explosion limit (LEL,=1.2 vol %) of hexane. Thus, it is appreciated that optical sensor apparatus OS can be used for LEL detection applications.

Example 4

Figure 11:
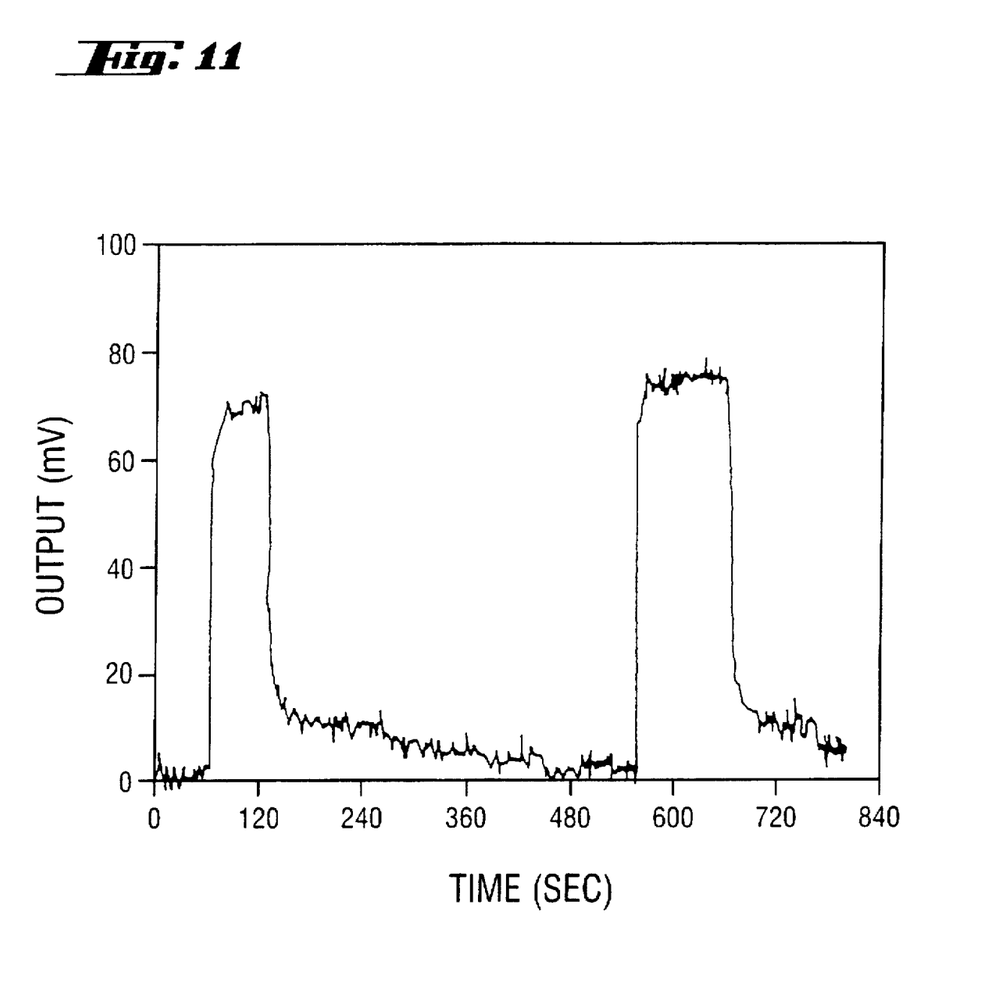
FIG. 11 is a graph showing an example of a fast response to the presence of a 100 ppm toluene vapor exhibited by the optical sensor apparatus of the present invention.

FIG. 11 is a graph showing that optical sensor apparatus OS exhibits a fast response to a 100 ppm toluene vapor under the same measurement conditions as in Example 1. Example 4 differs from Example 1 in that light source unit 2 used in Example 4 is a HeNe laser and that polymer thin film 10 has a thickness of 975 μm. Polymer thin film 10 was exposed to the 100 ppm toluene vapor for a short time and then to ambient air. Optical sensor apparatus OS responded in 1 or 2 seconds to the toluene vapor, and the output of the apparatus was returned to the original state in several minutes after the toluene vapor was replaced with ambient air.

In the foregoing embodiments and examples, an electric circuit for generating an electric signal indicative of the existence and/or concentration of an organic solvent vapor may be configured by a circuit composed of analog circuitries or by a circuit composed mainly of digital circuitries. Such electric circuits will be next described with reference to FIGS. 12A–12D.

Figure 12A:
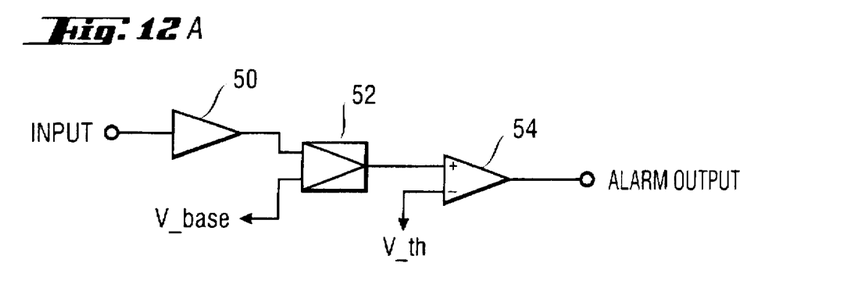
FIGS. 12A–12D are block circuit diagrams respectively showing an exemplary electric circuit for processing the output from a light detecting unit of the optical sensor apparatus according to the present invention.

The analog-based circuit may be implemented in several ways. FIG. 12A shows an example of a circuit for outputting an electric signal indicative of the existence of an organic solvent vapor. A signal from light detecting unit 4 is subjected to impedance conversion and amplification in a pre-amplifier 50, and then supplied to a difference calculating circuit 52. Difference calculating circuit 52 subtracts a voltage V_base corresponding to zero concentration from the output of pre-amplifier 50 to generate a voltage corresponding to a difference from the zero concentration. This voltage is compared with a comparison level V_th in a comparator circuit 54 which in turn generates an alarm signal at high level when the voltage is higher than the comparison level V_th and at low level when it is lower than V_th.

Figure 12B:
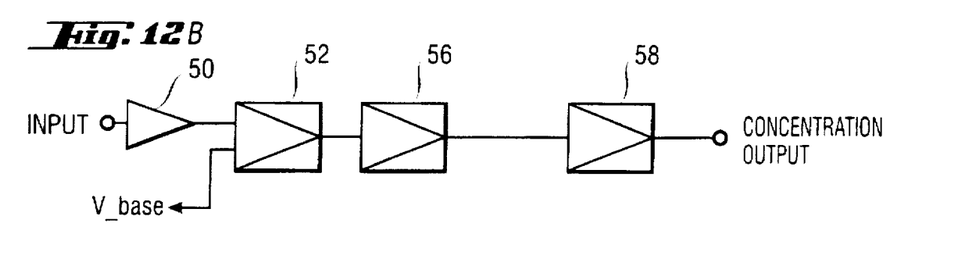

FIG. 12B shows an example of a circuit for outputting an electric signal indicative of a concentration of an organic solvent vapor. Since a circuit portion from the input up to difference calculating circuit 52 is the same as that in FIG. 12A, an explanation thereof will be omitted. The output of difference calculating circuit 52 is supplied to a linearizing circuit 56 which operates, when the output of light detecting unit 4 is not in a proportional relationship with the concentration, to convert the output to a voltage proportional to the concentration. The output of linearizing circuit 56 is coupled to an output circuit 58 which converts a signal inputted thereto to an analog signal of an appropriate form. The outputted analog signal may have a value within a concentration measuring range corresponding to 1–5 V, 4–20 mA, 0–10 mV, 0–1 V, and so on.

Figure 12C:
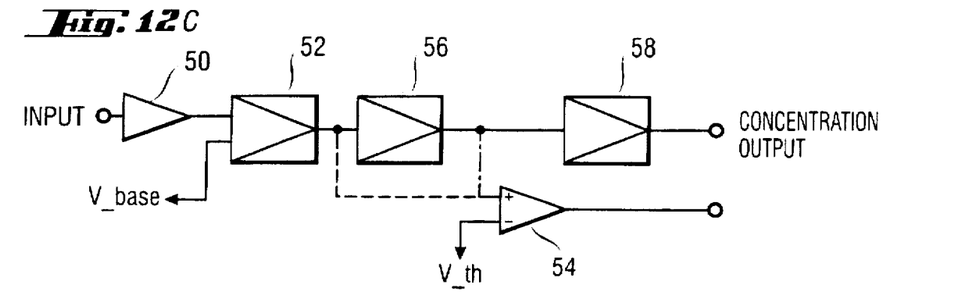

FIG. 12C shows an example of a circuit for outputting both an electric signal indicative of the existence of an organic solvent vapor and an electric signal indicative of the concentration thereof. Since this circuit is a combination of the circuits shown in FIGS. 12A and 12B, an explanation thereof will be omitted. It should be noted in FIGS. 12C that a signal supplied to a non-inverting input of a comparator 54 may be the output of linearizing circuit 56 as indicated by a one-dot chain line or the output of difference calculating circuit 52 as indicated by a dotted line.

Figure 12D:
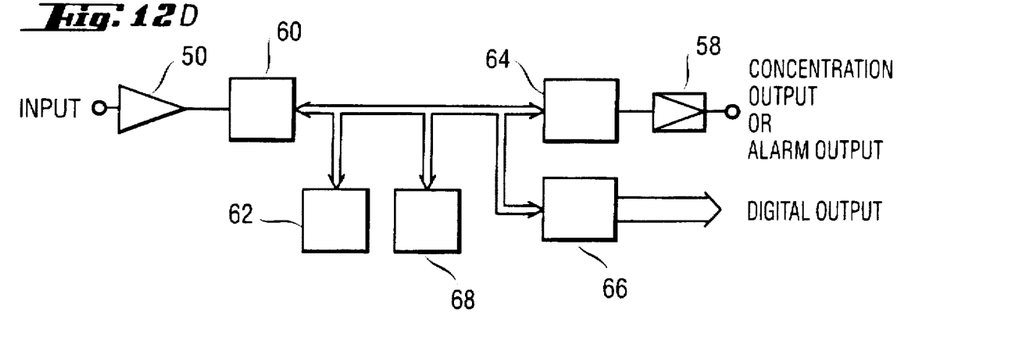

When the signal generating circuit is implemented in a digital form, a microcomputer may be employed. FIG. 12D shows an example of such a microcomputer-based digital circuit. The output of pre-amplifier 50 is directly supplied to an A/D (analog-to-digital) convertor 60 to be converted to digital data. The digital date then undergoes a variety of operations identical to those performed in the above-mentioned analog circuits, executed by a microcomputer 62 in a software manner. The output from the circuit shown in FIG. 12D may be in either of analog or digital form. When the output is delivered in an analog form, the output of microcomputer 62 is converted to an analog electric signal by a D/A (digital-to-analog) convertor 64 and outputted through an output circuit 58 as a concentration signal proportional to a detected concentration of an organic solvent vapor or an alarm signal informing the existence of the same. Conversely, when the output is delivered in a digital form, the output from microcomputer 62 is delivered through a digital output circuit 66. This digital output may be a serial output in accordance with RS5232C or the like or a parallel output in accordance with GRIB or the like. Microcomputer 62 is connected to a memory 68 for storing the outputs of microcomputer 62 as well as for serving as a storage for other data.

As is apparent from the foregoing detailed description based on several embodiments, the present invention is particularly advantageous in that it provides an optical sensor apparatus for detecting the existence and/or concentration of a vapor of an organic solvent, which is simple in structure, easy to manufacture, and highly reliable. In addition, the optical sensor apparatus is inexpensive and portable, and can be reduced in size and weight.

We claim:

1. An optical sensor apparatus utilizing an interference enhance reflection (IER) method for optically detecting at least one of the existence and the concentration of a vapor of an organic solvent, comprising:

a light source unit;

a sensing element comprising a polymer thin film formed on a flat reflecting plate and irradiated by the light emitted from said light source unit, said thin film changing a product of the thickness and the refractive index thereof when making contact with the vapor of the organic solvent;

a light detecting unit for detecting the light reflected by said sensing element; and a housing for supporting said light source unit, said sensing element and said light detecting unit.

2. An apparatus as set forth in claim 1, wherein said housing holds said light source unit and the light detecting unit to face said sensing element so that the light from said light source unit impinges upon said polymer thin film at an incident angle less than 90 degrees and that the light reflected from said polymer thin film is detected by said light detecting unit.

3. An apparatus as set forth in claim 1, wherein said light source unit comprises a light emitting member, a first optical fiber having one end connected to said light emitting member for transmitting the light emitted from said light emitting member and an irradiating member connected to the other end of said first optical fiber for irradiating said polymer thin film, and wherein said light detecting unit comprises a light reception member for receiving the light reflected from said polymer thin film, a second optical fiber having one end thereof connected to said light reception member for transmitting the light received by said light reception member and a light detector connected to the other end of said second optical fiber.

4. An apparatus as set forth in claim 3, wherein a light irradiating portion of said first optical fiber and a light receiving portion of said second optical fiber are joined integrally or identical.

5. An apparatus as set forth in claim 1, wherein said housing comprises a vapor inlet for introducing said vapor of the organic solvent, a vapor outlet for exhausting said vapor of the organic solvent and a passage interconnecting said vapor inlet and said vapor outlet for causing the vapor to make contact with said polymer thin film.

6. An apparatus as set forth in claim 1 further comprising an electronic circuit for producing an electric signal representing at least one of the existence and concentration of the vapor of the organic solvent.

\* \* \* \* \*